United States Patent
Lubda et al.

(10) Patent No.: US 11,246,935 B2
(45) Date of Patent: Feb. 15, 2022

(54) PARTICLE SIZE AND DISTRIBUTION OF POLYMER FOR MELT EXTRUSION APPLICATION

(71) Applicant: MERCK PATENT GMBH, Darmstadt (DE)

(72) Inventors: Dieter Lubda, Bensheim (DE); Mengyao Zheng, Bensheim (DE); Nicole Di Gallo, Bensheim (DE); Anja-Nadine Knuettel, Mannheim (DE)

(73) Assignee: MERCK PATENT GMBH, Darmstadt (DE)

( * ) Notice: Subject to any disclaimer, the term of this patent is extended or adjusted under 35 U.S.C. 154(b) by 168 days.

(21) Appl. No.: 16/301,181

(22) PCT Filed: May 10, 2017

(86) PCT No.: PCT/EP2017/061130
§ 371 (c)(1),
(2) Date: Nov. 13, 2018

(87) PCT Pub. No.: WO2017/194578
PCT Pub. Date: Nov. 16, 2017

(65) Prior Publication Data
US 2019/0111138 A1     Apr. 18, 2019

(30) Foreign Application Priority Data
May 13, 2016  (EP) .................... 16169690

(51) Int. Cl.
A61K 47/32   (2006.01)
A61K 45/06   (2006.01)
B29C 48/00   (2019.01)
C08L 29/04   (2006.01)
A61K 9/14    (2006.01)
C08K 5/00    (2006.01)
B29K 29/00   (2006.01)

(52) U.S. Cl.
CPC .............. *A61K 47/32* (2013.01); *A61K 9/146* (2013.01); *A61K 45/06* (2013.01); *B29C 48/022* (2019.02); *C08K 5/005* (2013.01); *C08K 5/0016* (2013.01); *C08L 29/04* (2013.01); *B29K 2029/04* (2013.01); *C08L 2203/02* (2013.01)

(58) Field of Classification Search
CPC ........................................ A61K 47/32
See application file for complete search history.

(56) References Cited

U.S. PATENT DOCUMENTS

| | | | |
|---|---|---|---|
| 4,849,256 A * | 7/1989 | Newman | .......... C08J 3/124 427/202 |
| 4,954,567 A | 9/1990 | Oishi et al. | |
| 5,456,923 A | 10/1995 | Nakamichi et al. | |
| 8,486,423 B2 | 7/2013 | Brough et al. | |
| 9,339,440 B2 | 5/2016 | Brough et al. | |
| 10,449,547 B2 * | 10/2019 | Grassano | ................. B29B 7/20 |
| 10,828,258 B2 | 11/2020 | Ognibene et al. | |
| 2010/0120924 A1 | 5/2010 | Uramatsu et al. | |
| 2012/0107408 A1 * | 5/2012 | Ausborn | ............. A61K 9/1647 424/501 |
| 2018/0207101 A1 | 7/2018 | Ognibene et al. | |
| 2019/0125681 A1 | 5/2019 | Albed Alhnan | |
| 2019/0175543 A1 | 6/2019 | Staric et al. | |

FOREIGN PATENT DOCUMENTS

| | | |
|---|---|---|
| CN | 101835492 B | 11/2012 |
| DE | 3811201 A1 | 12/1988 |
| DE | 102007026166 A1 | 12/2008 |
| EP | 2105130 A1 | 9/2009 |
| WO | 15011113 A1 | 1/2015 |
| WO | 16015813 A1 | 2/2016 |
| WO | 16015814 A1 | 2/2016 |
| WO | 16038356 A1 | 3/2016 |

OTHER PUBLICATIONS

DIN 53015 dated Feb. 2001 (pp. 1-16). Published by DIN Deutsches Institutfur Normung, Berlin.
International Search Report PCT/EP2017/061130 dated Aug. 28, 2017 (pp. 1-2).
Chiou W. L.; Riegelman S.: "Pharmaceutical applications of Solid dispersion systems", J. Pharm Sci, vol. 60, No. 9, 1971, p. 1281.
Sinswat P. et al.: "Stabilizer choice for rapid dissolving high potency itraconazole particles formed by evaporative precipitation into aqueous solution", Int. J. of Pharmaceutics, vol. 302, 2005, pp. 113-124, XP005017012 (Abstract).
Dinunzio J.C. et al.: "III Amorphous compositions using concentration enhancing polymers for improved bioavailability of itraconazole", Molecular Pharmaceutics, vol. 5, No. 6, 2008, pp. 968-980, XP008178189 (Abstract).
Breitenbach J: "Melt extrusion: from process to drug delivery technology ", Eur. J. Pharm. Biopharm., vol. 54, 2002, pp. 107-117, XP004377352 (Abstract).

(Continued)

*Primary Examiner* — Kyle A Purdy
(74) *Attorney, Agent, or Firm* — Millen White Zelano and Branigan, PC; Csaba Henter

(57) ABSTRACT

An extrudable polyvinyl alcohol (PVA) powder with improved flowability containing particles of PVA, which has been cryo-milled, and which has $d_{50}$ particle sizes in the range of 45 to 1400 µm; or which has a particle size distribution of $d_{10}$=20±10 µm, $d_{20}$=30±10 µm, $d_{50}$=70±10 µm, $d_{90}$=200±30 µm, and $d_{99}$=300±30 µm; and a powdery composition for the preparation of pharmaceutical formulations which contains the polyvinyl alcohol homogeneously mixed with at least one active pharmaceutical ingredient (API); and a process for producing a solid pharmaceutical dosage form by extruding or forming a homogeneous melt of a mixture of ingredients containing the powdered polyvinyl alcohol and at least one active pharmaceutical ingredient (API), and forming a powder or a molded form.

21 Claims, 5 Drawing Sheets

(56) References Cited

OTHER PUBLICATIONS

Schilling S. U. et al.: "Citric acid as a solid-state plasticizer for Eudragit RS PO", J. Pharm. Pharmacol., vol. 59, No. 11, 2007, pp. 1493-1500 (Abstract).
DIN53015.
W. De Jaeghere et al.: "Hot-melt extrusion of polyvinyl alcohol for oral immediate release applications", International Journal of Pharmaceutics, vol. 492, No. 1-2, Aug. 1, 2015 (Aug. 1, 2015), Amsterdam, NL, pp. 1-9, XP055397004, ISSN: 0378-5173.
Colin P Derdeyn et al: "Polyvinyl Alcohol Particle Size and Suspension Characteristics", AJNR AM J Neuroradiol, vol. 16, Jun. 30, 1995 (Jun. 30, 1995), pp. 1335-1343, XP055397013.
Bowen P: "Particle Size Distribution Measurement from Millimeters to Nanometers and from Rods to Platelets", Journal of Dispersion Science and Technol, Taylor and Francis Group, New York, NY, US, vol. 23, No. 5, Jan. 1, 2002 (Jan. 1, 2002), pp. 631-662, XP009102859, ISSN: 0193-2691.
Office Action in corresponding Japanese Patent Application No. 2018-559869 dated Mar. 6, 2021 (pp. 1-9 ) and english translation thereof (pp. 1-11).

\* cited by examiner

PARTICLE SIZE AND DISTRIBUTION OF POLYMER FOR MELT EXTRUSION APPLICATION

The present invention relates to an improved powdered polyvinyl alcohol (PVA), and that due to its improved properties can be better dosed during formulation processes. Furthermore, this invention refers to pharmaceutical formulations comprising polyvinyl alcohol as carrier matrix and their use.

TECHNICAL FIELD

In order to achieve a more consistent dosage rate of the active ingredient in pharmaceutical formulations, it is useful when the active ingredient is present as a homogeneous dispersion or solution in carrier.

Solid dispersions are defined as being a dispersion of one or more active ingredients in an inert solid matrix and can broadly classified as those containing a drug substance in the crystalline state or in the amorphous state [Chiou W. L., Riegelman S. Pharmaceutical applications of Solid dispersion systems; J. Pharm Sci. 1971, 60 (9), 1281-1301]. Solid dispersions containing pharmaceutical active ingredients in the crystalline state provide dissolution enhancement by simply decreasing surface tension, reducing agglomeration, and improving wettability of the active substance [Sinswat P., et al.; Stabilizer choice for rapid dissolving high potency itraconazole particles formed by evaporative precipitation into aqueous solution; Int. J. of Pharmaceutics, (2005) 302; 113-124]. While crystalline systems are more thermodynamically stable than their amorphous counterparts, the crystalline structure must be interrupted during the dissolution process, requiring energy. Solid dispersions containing an active ingredient, this means a drug, dissolved at the molecular level, known as amorphous solid solutions, can result in a significant increase in dissolution rate and extent of supersaturation [DiNunzio J. C. et al. III Amorphous compositions using concentration enhancing polymers for improved bioavailability of itraconazole; Molecular Pharmaceutics (2008); 5(6):968-980]. While these systems have several advantages, physical instability can be problematic due to molecular mobility and the tendency of the drug to recrystallize. Polymeric carriers with high glass transition temperatures seem to be well suited to stabilize these systems by limiting molecular mobility.

As such, solid dispersions can be created by a number of methods, including, but not limited to, spray-drying, melt extrusion, and thermokinetic compounding.

Although hot melt extrusion, a fusion processing technique, has been used in the food and plastics industry for more than a century, it has only recently gained acceptance in the pharmaceutical industry for the preparation of formulations comprising active ingredients processed by extrusion. And now, hot melt extrusion (HME) has been introduced as pharmaceutical manufacturing technology and has become a well-known process with benefits like continuous and effective processing, limited number of process steps, solvent free process etc. During hot melt extrusion mixtures of active ingredients, thermoplastic excipients, and other functional processing aids, are heated and softened or melted inside of an extruder and extruded through nozzles into different forms.

In this method, a thermoplastic carrier may be mixed with a pharmaceutical active substance and optional inert excipients and further additives. The mixture is fed into rotating screws that convey the powder into a heated zone where shear forces are imparted into the mixture, compounding the materials until a molten mass is achieved.

For an amorphous dispersion via melt extrusion, the polymeric carrier vehicle must first possess a thermoplasticity that allows the polymer to be passed through the extruder, and on the other hand the carrier must be thermally stable at barrel temperatures above the glass transition temperature or melting point of the polymer.

During hot melt extrusion the active ingredients are mixed with and embedded in excipients, such as polymers and plasticizers. Furthermore, drug substances are exposed to elevated temperatures for a period of time. Although a variety of factors can affect the residence time distribution of an extruded substance, these times typically fall within the 1 to 2 min range (Breitenbach J., Melt extrusion: from process to drug delivery technology. Eur. J. Pharm. Biopharm. (2002), 54, 107-117).

A prolonged exposure to elevated temperatures can induce decomposition of thermally labile compounds or accelerate decomposition of chemically unstable compounds. But the addition of processing aids, such as plasticizers, may allow processing to be carried out at a lower temperature (Schilling S. U. et al.; Citric acid as a solid-state plasticizer for Eudragit RS PO; J. Pharm. Pharmacol. (2007), 59(11), 1493-1500).

Therefore, as carriers for the application of (hot) melt extrusion, the polymers should have suitable properties, such as thermoplasticity, suitable glass transition temperature or melting point, thermostability at required processing temperature, no unexpected chemical interaction with active ingredients etc. In this context, polyvinyl alcohol (PVA) is an excellent compound, which is suitable for (hot) melt extrusion, as carrier for pharmaceutically active ingredients. Polyvinyl alcohol (PVA) is a synthetic water-soluble polymer that possesses excellent film-forming, adhesive, and emulsifying properties. It is prepared from polyvinyl acetate, where the functional acetate groups are either partially or completely hydrolyzed to alcohol functional groups. As the degree of hydrolysis increases, the solubility of the polymer in aqueous media increases, but also the crystallinity of the polymer increases. In addition to this, the glass transition temperature varies depending on its degree of hydrolysis. For example, a 38% hydrolyzed material has no melting point, but a glass transition temperature of approximately 48° C., whereas a 75-88% hydrolyzed material has a melting temperature of approximately 190-200° C.

Polyvinyl alcohol is soluble in water, but almost insoluble in almost all organic solvents, excluding, in some cases, in ethanol. This aspect of the polymer makes it very difficult to form amorphous and solid dispersions through spray drying when the drug has also a limited solubility in aqueous media.

U.S. Pat. No. 5,456,923 A provides a process for producing a solid dispersion, which overcomes disadvantages of the conventional production technology for solid dispersions. The process comprises employing a twin-screw extruder in the production of a solid dispersion. In accordance with this, a solid dispersion can be expediently produced without heating a drug and a polymer up to or beyond their melting points and without using an organic solvent for dissolving both components and the resulting solid dispersion has excellent performance characteristics. The process claims a polymer that is natural or synthetic and can be employed as a raw material where the polymer's functions are not adversely affected by passage through the twin screw extruder.

EP 2 105 130 A1 describes a pharmaceutical formulation comprising a solid dispersion having an active substance embedded in a polymer in amorphous form, and an external polymer as a recrystallization inhibitor independently of the solid dispersion. The external polymer is claimed as a solution stabilizer. The active substance should be sparingly soluble or less sparingly soluble in water. Thermoplastic polymers are claimed as drug carriers to form a solid dispersion. It is claimed that the solid dispersion is obtained by melt extrusion. The process comprises melting and mixing the polymer and the active ingredient, cooling, grinding, mixing with the external polymer, and producing a pharmaceutical formulation. It is claimed that the melting is carried out at a temperature below the melting point of the drug. It is also claimed that the melting is carried out at a temperature above the $T_g$ or melting point of the polymer, but from 0.1-5° C. below the melting point of the API. The melting point of pharmaceutical grades of PVA is normally above 178° C., although the glass transition temperature is in the range of 40-45° C.

Problem to be Solved

For preparation of pharmaceutical formulations it is a common method to homogenize the required ingredients with each other by extrusion. But because of the already above-described problematic chemical and physical properties of polyvinyl alcohol (PVA), it is difficult to dose uniformly PVA together with the other ingredients into an extruder, without that the supply of material is blocked, resulting in an interruption of the production process.

Accordingly, high demands are made on both the fluidity of the PVAs used as a carrier material but also on that of the mixture comprising the pharmaceutically active substance used for the extrusion process.

Therefore, it is object of the present invention to provide a PVA grade, which has improved physical properties which in turn, also improves the flowability of mixtures of this PVA grade together with active ingredients and optionally further additives, so that a continuous dosing into the feeder of an extruder is made possible without any interruption.

Particularly, it is therefore an object of the present invention to provide a PVA, that can be dosed uniformly into an extruder together with the active substances, and optionally with other ingredients, and which allows the formulation of homogeneous mixtures containing active ingredients (APIs).

Another object of this invention is to provide improved PVA(s) in a form which allows that the polymer can be melt extruded without addition of significant amounts of additives.

SUMMARY OF THE INVENTION

Surprisingly it was found by experiments for the preparation of pharmaceutical formulations, that extrudable polyvinyl alcohol (PVA) powder shows improved flowability, which is cryo-milled and which has particle sizes in the range of 45 to 1400 µm, preferably in the range of 45 to 1000 µm, most preferred in the range of 50 to 300 µm. In particular, these improved properties are found for polyvinyl alcohol (PVA), having a particle size distribution of $d_{10}=20\pm10$ µm, $d_{20}=30\pm10$ µm, $d_{50}=70\pm10$ µm, $d_{90}=200\pm30$ µm, $d_{99}=300\pm30$ µm and wherein optionally the particle size distribution is adjusted by combining respective sieve fractions. PVA, showing these properties is hot melt extrudable or melt extrudable. In particular, it was found, that polyvinyl alcohol grades, which are showing these properties, are those having viscosities ≤40 mPa·s, whereby the viscosity being measured on 4% aqueous solution at 20° C. (DIN 53015).

These particular polyvinyl grades fulfilling said conditions are preferably selected preferably from the group: PVA 3-80, PVA 3-85, PVA 3-88, PVA 3-98, PVA 4-88, PVA 4-98, PVA 5-74, PVA 5-82, PVA 6-88, PVA 6-98, PVA 8-88, PVA 10-98, PVAPVA 13-88, PVA 15-99, PVA 18-88, PVA 20-98, PVA23-88, PVA 26-80, PVA 26-88, PVA28-99, PVA 30-98, PVA 30-92, PVA 32-88, PVA 40-88, most preferred from the group: PVA 3-88, PVA 4-88, PVA 5-74, PVA 5-88, PVA 8-88, and PVA 18-88.

Accordingly, a PVA grade is subject matter of the present invention, which is suitable as carrier for the preparation of pharmaceutical formulations and which is a milled pharmaceutical grade powder showing an improved flowability enabling an uninterrupted feeding and dosing during processing. In one embodiment of the invention polyvinyl alcohol as described above is homogeneously mixed with at least one active pharmaceutical ingredient, whereby this mixture is storage and transport-stable, and shows an improved flowability which leads to an uninterrupted feeding and dosing during processing. This powdery composition may comprise at least one additive selected from the group plasticizers, surface active materials, antioxidants, stabilizing agents, solubility-enhancing agents, pH control agents and flow regulators.

In a further embodiment of the invention the powdery composition of the present invention is a milled powder comprising polyvinyl alcohol and optionally one or more further excipient(s) with particle sizes in the range of 45 µm to 1400 µm, preferably in the range of 45 to 1000 µm, most preferred in the range of 50 to 300 µm. In particular, it is a milled powder comprising polyvinyl alcohol and optionally one or more further excipient(s) having a particle size distribution of $d_{10}=20\pm10$ µm, $d_{20}=30\pm10$ µm, $d_{50}=70\pm10$ µm, $d_{90}=200\pm30$ µm, $d_{99}=300\pm30$ µm.

Thus, the present invention also consists in a method for producing the PVA powder according to the invention with improved properties for the manufacture of pharmaceutical formulations, in particular for the production of extruded formulations. Said method or process for producing a solid pharmaceutical dosage form is characterized in that the mixture of ingredients including the powdered polyvinyl alcohol or including the powdery composition as characterized above is processed in an extruder to a homogeneous melt, and that then the feeds are shaped either to a powder or to molded forms.

The particular advantage of the present invention is that the process can be carried out continuously, in that the mixture of ingredients including the powdered polyvinyl alcohol having the improved properties is evenly fed into the feeder line of the extruder and that it is processed to a homogeneous melt, and that the feed is then shaped. The process according to the present invention includes the steps of a) cryo-milling polyvinyl alcohol (PVA) to a powder having particle sizes in the range of 45 to 1400 µm, preferably in the range of 45 to 1000 µm, most preferred in the range of 50-300 µm, and b) mixing this powder homogeneously with at least one active pharmaceutical ingredient, and optionally with at least one additive selected from the group plasticizer, surface active material, antioxidant, stabilizing agent, solubility-enhancing agents, pH control agents and flow regulators and c) feeding this powdery composition evenly into the feeder line of the extruder followed by processing to a homogeneous melt, and shaping this feed.

This process can be performed particularly well, if in step a) polyvinyl alcohol (PVA) is milled to a powder having a particle size distribution of $d_{10}=20\pm10$ µm, $d_{20}=30\pm10$ µm, $d_{50}=70\pm10$ µm, $d_{90}=200\pm30$ µm, $d_{99}=300\pm30$ µm, namely when solid polyvinyl alcohol (PVA) having pharmaceutical grade is applied which is characterized having a viscosity ≤40 mPa·s, the viscosity being measured on 4% aqueous solution at 20° C. DIN 53015, is milled to a powder having a particle size distribution of $d_{10}=20\pm10$ µm, $d_{20}=30\pm10$ µm, $d_{50}=70\pm10$ µm, $d_{90}=200\pm30$ µm, $d_{99}=300\pm30$ µm, and wherein optionally the particle size distribution is adjusted by combining respective sieve fractions. In this case very particularly preferred is the use of polyvinyl alcohol (PVA), selected from the group: PVA 3-80, PVA 3-85, PVA 3-88, PVA 3-98, PVA 4-88, PVA 4-98, PVA 5-74, PVA 5-82, PVA 6-88, PVA 6-98, PVA 8-88, PVA 10-98, PVAPVA 13-88, PVA 15-99, PVA 18-88, PVA 20-98, PVA23-88, PVA 26-80, PVA 26-88, PVA28-99, PVA 30-98, PVA 30-92, PVA 32-88, PVA 40-88, most preferred from the group: PVA 3-88, PVA 4-88, PVA 5-74, PVA 5-88, PVA 8-88, and PVA 18-88, which is milled to a powder having a particle size distribution of $d_{10}=20\pm10$ µm, $d_{20}=30\pm10$ µm, $d_{50}=70\pm10$ µm, $d_{90}=200\pm30$ µm, $d_{99}=300\pm30$ µm, and wherein optionally the particle size distribution is adjusted by combining respective sieve fractions.

Thus, a solid pharmaceutical dosage form, which is characterized as disclosed herein and which is obtainable by a process as characterized here, is the subject of the present invention. By making available this solid formulation disadvantages as described above can be overcome in a simple manner.

DETAILED DESCRIPTION OF THE INVENTION

Figure 1:
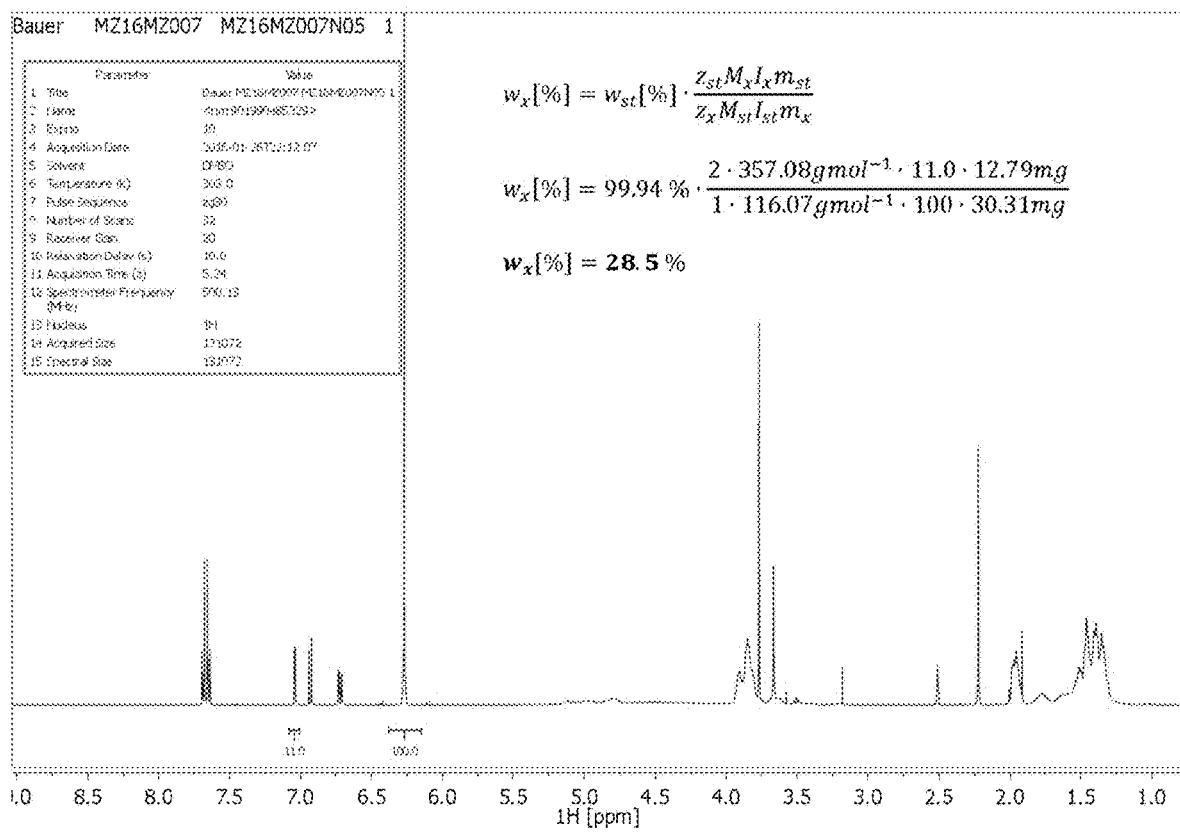
FIG. 1: shows a NMR spectrogram of 20 mg indomethacin and 20 mg maleic acid in DMSO-d6

While the making and using of various embodiments of the present invention are discussed in detail below, it should be appreciated that the present invention provides more applicable inventive concepts than described here in detail. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "a homogenous melt, or mixture or form" refers to the various compositions that can be made by extruding the made-up source material, which is prepared by milling and combining selected sieve fractions.

As used herein, the term "heterogeneously homogeneous composite" refers to a material composition having at least two different materials that are evenly and uniformly distributed throughout the volume and which are prepared of the one or more APIs and the one or more pharmaceutically acceptable excipients, including a pretreated PVA into a composite.

As used herein, "bioavailability" is a term meaning the degree to which a drug becomes available to the target tissue after being administered to the body. Poor bioavailability is a significant problem encountered in the development of pharmaceutical compositions, particularly those containing an active ingredient that is not highly soluble.

As used herein, the phrase "pharmaceutically acceptable" refers to molecular entities, compositions, materials, excipients, carriers, and the like that do not produce an allergic or similar untoward reaction when administered to humans in general.

As used herein, "pharmaceutically acceptable carrier" or "pharmaceutically acceptable materials" includes any and all solvents, dispersion media, coatings, antibacterial and antifungal agents, isotonic and absorption delaying agents, and the like. The use of such media and agents for pharmaceutical active substances is well known in the art.

The API (active pharmaceutical ingredient) may be found in the form of one or more pharmaceutically acceptable salts, esters, derivatives, analogs, prodrugs, and solvates thereof. As used herein, a "pharmaceutically acceptable salt" is understood to mean a compound formed by the interaction of an acid and a base, the hydrogen atoms of the acid being replaced by the positive ion of the base.

As used herein, "poorly soluble" refers to having a solubility means the substance needs 100 ml solvent to dissolve 1 g substance.

For the characterizing particle sizes "mean" or "average particle sizes" ($d_{50}$) are given. These values are assessed by means of sieve analysis using wire mesh plates. Sieve plates are arranged from largest aperture to smallest, and the particle size is assessed based on proportion of material caught at each level. All sieve plates have apertures with square cross sections. The mean particle size ($d_{50}$) is then calculated from the sieving results. $d_{50}$ is defined as the equivalent diameter where 50% of the mass (of particles) of the sampled powder has a smaller diameter, and thus 50% of the material remains coarser. $d_{50}$ can therefore be described as the average particle size.

As used herein, "derivative" refers to chemically modified inhibitors or stimulators that still retain the desired effect or property of the original API. Such derivatives may be derived by the addition, removal, or substitution of one or more chemical moieties on the parent molecule. Such moieties may include, but are not limited to, an element such as a hydrogen or a halide, or a molecular group such as a methyl group. Such a derivative may be prepared by any method known to those of skill in the art. The properties of such derivatives may be assayed for their desired properties by any means known to those of skill in the art. As used herein, "analogs" include structural equivalents or mimetics.

A variety of administration routes are available for delivering the APIs to a patient in need. The particular route selected will depend upon the particular drug selected, the weight and age of the patient, and the dosage required for therapeutic effect. The pharmaceutical compositions may conveniently be presented in unit dosage form. The APIs suitable for use in accordance with the present disclosure, and their pharmaceutically acceptable salts, derivatives, analogs, prodrugs, and solvates thereof, can be administered alone, but will generally be administered in admixture with a suitable pharmaceutical excipient, diluent, or carrier selected with regard to the intended route of administration and standard pharmaceutical practice.

The APIs may be used in a variety of application modalities, including oral delivery as tablets, capsules or suspensions; pulmonary and nasal delivery; topical delivery as emulsions, ointments or creams; transdermal delivery; and parenteral delivery as suspensions, microemulsions or depot. As used herein, the term "parenteral" includes subcutaneous, intravenous, intramuscular, or infusion routes of administration.

The solution agent used in the solution can be an aqueous such as water, one or more organic solvents, or a combination thereof. When used, the organic solvents can be water miscible or non-water miscible. Suitable organic solvents include but are not limited to ethanol, methanol, tetrahydrofuran, acetonitrile, acetone, tert.-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, and combinations thereof.

The excipients and adjuvants that may be used in the presently disclosed compositions and composites, while potentially having some activity in their own right, for example, antioxidants, are generally defined for this application as compounds that enhance the efficiency and/or efficacy of the effective ingredients. It is also possible to have more than one effective ingredient in a given solution, so that the particles formed contain more than one effective ingredient.

As stated, excipients and adjuvants may be used to enhance the efficacy and efficiency of the APIs.

Thermal binders may also be used in the presently disclosed compositions and composites.

Depending on the desired administration form the formulations can be designed to be suitable in different release models, which are well known to the skilled person, as there are: immediate, rapid or extended release, delayed release or for controlled release, slow release dosage form or mixed release, including two or more release profiles for one or more active pharmaceutical ingredients, timed release dosage form, targeted release dosage form, pulsatile release dosage form, or other release forms.

The resulting composites or compositions disclosed herein may also be formulated to exhibit enhanced dissolution rate of a formulated poorly water soluble drug.

The United States Pharmacopeia-National Formulary mandates that an acceptable polyvinyl alcohol for use in pharmaceutical dosage forms must have a percentage of hydrolysis between 85 and 89%, as well as a degree of polymerization between 500 and 5000. The degree of polymerization (DM) is calculated by the equation:

$$DM = (\text{Molar Mass})/((86)-(0{,}42(\text{the degree of hydrolysis})))$$

The European Pharmacopoeia mandates that an acceptable polyvinyl alcohol for use in pharmaceutical dosage forms must have an ester value no greater than 280 and a mean relative molecular mass between 20,000 and 150,000. The percentage of hydrolysis (H) can be calculated from the following equation:

$$H = ((100-(0{,}1535)(EV))/(100-(0{,}0749)(EV))) \times 100$$

Where EV is the ester value of the polymer. Thus, only polymers with a percentage of hydrolysis greater than 72.2% are acceptable according to the European Pharmacopoeia monograph.

As already mentioned above, commercial polyvinyl alcohols in particulate form have poor flow behavior, especially if they are characterized by low viscosities (measured in a 4% aqueous solution at 20° C.). Accordingly, these powders have no continuous trouble-free flow. However, the latter is a prerequisite for a uniform feed to the processing of such powder materials.

Theoretically, powders, whose particle shapes are rather round and spherical, in general have the best flow behavior. Accordingly, in the past, attempts have been made to produce polyvinyl alcohol powders already directly by its synthesis with spherical particles. For example, from DE 38 11 201A a method is known for producing of spherical particles by suspension polymerization. However, this reaction requires a special adjustment of the reaction conditions. In addition, this reaction has to be followed by a hydrolysis reaction. With different particle sizes, it is difficult to achieve a uniform degree of hydrolysis of the polymer particles. By this method, polyvinyl alcohol powders are produced having viscosities of 80 mPa·s or higher.

Therefore, for the production of polyvinyl alcohol powders, which are comparable with those of the present invention, this method provides no alternative, especially as here PVA grades are desirable having viscosities of ≤40 mPa·s.

Now, it was found that these polyvinyl alcohol grades having viscosities of ≤40 mPa·s are also suitable to be manufactured by melt extrusion if they are pretreated as disclosed in the following and a homogenously dispersed solid solution of pharmaceutical active ingredient in polyvinyl alcohol can be produced by extrusion and the applied PVA powder can be fed without problems into the feeder.

In this way also poorly soluble pharmaceutical active ingredients (from BCS class II and IV) can be homogeneously mixed with PVA to build a solid dispersion. Furthermore, it was found by experiments that PVA in the different degrees of hydrolysis having viscosities of ≤40 mPa·s can be homogeneously mixed by melt extrusion with poorly soluble active ingredients, especially with PVA that is in accordance with the European Pharmacopoeia monograph and which is a pharmaceutically acceptable PVA with hydrolysis grades greater than 72.2%, and especially which includes grades of PVA that are pharmaceutically acceptable by either the USP (hydrolysis between 85-89%) or Ph. Eur. (hydrolysis grades greater than 72.2%). These PVA qualities have a molecular weight in the range of 14,000 g/mol to 250,000 g/mol.

Powdery compositions according to the invention may comprise at least a biologically active ingredient combined with a PVA that is pharmaceutically acceptable, which is combined with another pharmaceutically acceptable polymer. Such pharmaceutically acceptable polymer can also be selected from the group of hydrophilic polymers and can be a primary or secondary polymeric carrier that can be included in the composition disclosed herein and including polyethylene-polypropylene glycol (e.g. POLOXAMER™), carbomer, polycarbophil, or chitosan, provided that they are as free-flowing powder and are extrudable polymers. Hydrophilic polymers for use with the present invention may also include one or more of hydroxypropyl methylcellulose, carboxymethylcellulose, hydroxypropyl cellulose, hydroxyethyl cellulose, methylcellulose, natural gums such as gum guar, gum acacia, gum tragacanth, or gum xanthan, and povidone. Hydrophilic polymers also include polyethylene oxide, sodium carboxymethylcellulose, hydroxyethyl methyl cellulose, hydroxymethyl cellulose, carboxypolymethylene, polyethylene glycol, alginic acid, gelatin, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

In general, it must be considered that there are special requirements for polymers used as hot melt extrusion excipients:

The polymer must be thermoplastic, must have a suitable glass transition temperature and a high thermal stability. The polymer must have no toxic properties and must have a high biocompatibility, etc. Therefore, pharmaceutical grades of polyvinyl alcohol (PVA), which are chosen here for the preparation of formulations comprising active ingredients by hot melt extrusion, are those having a low viscosity.

Polyvinyl alcohol (PVA) is a synthetic polymer, which is produced by polymerization of vinyl acetate and partial hydrolysis of the resulting esterified polymer. As already mentioned above, chemical and physical properties of polyvinyl alcohol, such as viscosity, solubility, thermal properties, etc. are very depending on its degree of polymerization, chain length of PVA polymer, and the degree of hydrolysis.

PVA can be used for the production of different formulations for various modes of administration to treat a variety of disorders. Accordingly, PVA is processed in a wide range of pharmaceutical dosage forms, including ophthalmic, transdermal, topical, and especially, oral application forms.

As mentioned above, it is for the successful industrial processing of a solid in an extrusion process also necessary that a uniform continuous metering is possible in the feed of the extruder.

We have found, that for this purpose, the solid must have suitable particle characteristics, including appropriate particle sizes, and flowability or fluidity.

It was also found through the experiments, that by the inventive pretreatment of appropriate commercially available PVA, optionally by blending with suitable ingredients, a stable product is obtained, which may be prepared as a ready-to-use product. Such a product can easily be loaded into the feeder of the extruder without any interruption and it makes the extrusion process feasible although a PVA is used as an excipient having a low viscosity of ≤40 mPa·s.

It was found, that an easily extrudable product can be obtained, when a commercially available PVA with pharma grade and low viscosity of ≤40 mPa·s is milled into fine powder and blended with ingredients.

The resulting mixture can be fed continuously without problems and without any halt into the feeder of an extruder.

Thus, the pretreatment of the applied PVA makes, that the extrusion process is feasible in a simple manner. In addition, it has been found, that not only the milling to a fine powder improves the uniform feeding of the PVA powder into the feeder of the extruder. Surprisingly, further significant improvement in the flowability of the milled polymer powder is achieved by sieving the milled polymer into various sieve fractions, and subsequent combining certain sieve fractions having specific grain sizes with each other. In summary, clearly defined particle sizes and size distributions result in PVA powders with significantly improved flowability and thus in an improved processability of the received PVA powders.

It was found, that milled polyvinyl alcohol powders of pharmaceutical grade to a powder as characterized above and having particle sizes in the range of 45 to 1400 µm, preferably in the range of 45 to 1000 µm, most preferred in the range of 50-300 µm show improved flowabilities.

In particular, these powders exhibit improved flow properties when the particle size distribution is in the range of $d_{10}=20\pm10$ µm, $d_{20}=30\pm10$ µm, $d_{50}=70\pm10$ µm, $d_{90}=200\pm30$ µm, $d_{99}=300\pm30$ µm, namely when solid polyvinyl alcohol (PVA) having pharmaceutical grade is applied which is characterized having a viscosity ≤40 mPa·s, the viscosity being measured on 4% aqueous solution at 20° C. DIN 53015. In this case very particularly preferred is the use of polyvinyl alcohol (PVA) having pharmaceutical grade, selected from the group: PVA 3-80, PVA 3-85, PVA 3-88, PVA 3-98, PVA 4-88, PVA 4-98, PVA 5-74, PVA 5-82, PVA 6-88, PVA 6-98, PVA 8-88, PVA 10-98, PVAPVA 13-88, PVA 15-99, PVA 18-88, PVA 20-98, PVA23-88, PVA 26-80, PVA 26-88, PVA28-99, PVA 30-98, PVA 30-92, PVA 32-88, PVA 40-88, most preferred from the group: PVA 3-88, PVA 4-88, PVA 5-74, PVA 5-88, PVA 8-88, and PVA 18-88, which is milled to a powder having a particle size distribution of $d_{10}=20\pm10$ µm, $d_{20}=30\pm10$ µm, $d_{50}=70\pm10$ µm, $d_{90}=200\pm30$ µm, $d_{99}=300\pm30$ µm, and wherein optionally the particle size distribution is adjusted by combining respective sieve fractions.

Powders, comprising particles larger than in the range of about 1400 µm, cannot be fed into the feeder, because of a lack of homogeneity of the mixture of ingredients and PVA particles, especially because they tend to stick and to agglomerate, but also they tend to separate out, because of the different sized ingredients that segregate.

A particularly troublesome problem in this case is that pharmaceutical active ingredients (APIs), which have smaller particle diameters, segregate during feeding, and in the following it is not any more possible to achieve a homogeneous distribution in the carrier polymer during extrusion.

Additionally, it is very difficult to control the feeding rate of the mixture with large polyvinyl alcohol particles. The particle size and distribution of polymer powders used as carrier is a significant parameter to influence the feasibility and accuracy of extruder feeding. On the other side, particle sizes lower than in the range given above, especially particle sizes lower than 45 µm, lead to issues of lack of flowability and feeder blocking. Therefore, in connection with the experiments carried out, it was found that it is advantageous to define a suitable particle size distribution for PVA, if it shall be applied as excipients in the production of pharmaceutical formulations, which are prepared by hot melt extrusion.

Here it has to be considered, that a continuous extrusion is only possible if the starting materials of the formulation can be metered uniformly. The latter is only possible if the applied PVA shows an adequate flowability, and if it is easy to load into the feeder, and shows good homogeneity together with active ingredients etc.

Examples

Even without any further explanations, it is assumed that a person skilled in the art can make use of the above description in its widest scope. The preferred embodiments and examples are therefore to be regarded merely as descriptive but in no way limiting disclosures.

For better understanding and for illustration, examples are given below which are within the scope of protection of the present invention. These examples also serve for the illustration of possible variants.

The complete disclosure of all applications, patents and publications mentioned above and below are incorporated by reference in the present application and shall serve in cases of doubt for clarification.

It goes without saying that, both in the examples given and also in the remainder of the description, the quoted percentage data of the components present in the compositions always add up to a total of 100% and not more. Given temperatures are measured in ° C.

Now, in order to carry out the following experiments a commercially available PVA is cryo-milled into three charges under different milling conditions (definition of method is following) to obtain different particle sizes and particle distributions of PVA powders:

Charge 1: Particle size in the range of <45 µm;
Charge 2: Particle size in the range of 45-1400 µm
Charge 3: Particle size in the range of >1400 µm The milled PVA powder is physically blended with active ingredients in an amount of 20-60% by weight, with or without additional plasticizers. The mixture of PVA powder is characterized regarding to the flowability, homogeneity and feasibility of feeding into the extruder feeder.

The analysis of the data obtained indicated, that cryo-milled PVA powders with particles having an average particle size of 63 µm and a particle distribution of $d_{10} < 17.25$ µm,
$d_{50} < 63.75$ µm
and
$d_{90} < 169.91$ µm are the most suitable PVA powders to be blended with active ingredients and are easy to be fed into the extruder without any blocking of the feeder. Powders of PVA particles in the C group are not suitable as matrix for melt extrusion due to the blocking of the extruder feeder and because of their inhomogeneity together with applied active ingredients. Powders of PVA particles lower than 45 µm are difficult to be loaded into the extruder feeder due to their bad flowability and due to their tendency to aggregate in the feeder.

Methods and Materials
1. Raw Materials and Manufacturing Method
1.1 Materials
Background:

At first, the mixture of HME excipients and ingredients should be fed into the feeder of the extruder unhindered.

To achieve the precise feeding rate, the feeder can also be combined with a computer to control the feeding accuracy of the powder. Therefore, the particle size and distribution is a significant parameter to influence the feasibility and accuracy of extruder feeding. As described above, the milled PVA makes the extrusion process feasible. This means, that the particle size and distribution should be clearly defined with a particle size distribution area. Particles larger than this area cannot be fed into the feeder, because the homogeneity of the ingredient/PVA mixture is a problem due to the segregation of API. Additionally, it is very difficult to control the feeding rate of the mixture with large PVA particles. On the other side, particle sizes lower than in this range have an issue with flowability and feeder blocking. Therefore, it is necessary to define suitable particle sizes and size distribution of PVA powders for their application as hot melt extrusion excipients, which have the benefits of good flowability, easy loading, good homogeneity with active ingredients etc.

Raw Material:
Poly vinyl alcohol 4-88, excipient EMPROVE® exp Ph Eur, USP, JPE, Article No. 1.41350, Merck KGaA, Darmstadt, Deutschland Raw Material PVA 4-88 for Milling:
This PVA types are as coarse—several millimeters in size: too big to load them into the extruder and difficult to formulate a homogenous solid dispersion system with active ingredients together.

1.2 Manufacturing Method (Milling Method)
Mill Equipment for PVA:
Aeroplex spiral jet mill, type 200 AS Hosokawa Alpine, Augsburg, Germany Mill Condition:
with liquid nitrogen as cold grinding. The desired particle size is produced empirically in particular by varying the grinding temperature, to control the particle size of PVA. The grinding conditions are varied until the desired particle size is obtained.

2. Experiments & Characterization Methods
2.1 Equipment for Analysis
Feeder 1 (Brabender® Mini-Compounder KETSE 12/36 D)
Instrument for Angle of repose DIN ISO 4324
Stirrer (not always necessary)
Glass Funnel
Device for closing or opening the output of the funnel (flap)
Transparent plastic receptacle (diameter 10 cm)
Measuring block (to measure the cone of the powder)
Stand with disk
Spirit level
Different sizes of sieves
2.2 Define Different Groups of Particle Sizes of PVA 4-88
Group A: PVA 4-88 Particle Size→<45 µm
($D_{10}=6.2$ µm/$D_{50}=27.99$ µm/$D_{90}=54.76$ µm)
Group B: PVA 4-88 Particle Size→45 µm-1400 µm
($D_{10}=17.25$ µm/$D_{50}=63.74$ µm/$D_{90}=169.91$ µm)
Group C: PVA 4-88 Particle Size→>1400 µm
2.3 Characterization Methods
2.3.1 Particle Size and Distribution Particle size determination by laser diffraction with dry dispersion: Mastersizer 2000 with dispersing Scirocco 2000 (Malvern Instruments Ltd. UK.), Provisions at 1, 2 and 3 bar backpressure; Evaluation Fraunhofer; Dispersant RI: 1,000, obscuration limits: 0.1-10.0%, Tray Type: General Purpose, Background Time: 7500 msec Measurement Time: 7500 msec, implementation in accordance with ISO 13320-1 and the details of the technical manual and the specifications of the equipment manufacturer; Information in Vol-%.

2.3.2. Angle of Repose (DIN ISO 4324)
The Angle of repose gives information about the flowability of the product for example in the feeder (HME), tablet press etc. First of all you have to adjust the disk (with the stand on it). To set up the equipment, proceed as the picture.

After that you can fill in your powder into the glass funnel (two-thirds). Attention: Ensure that the flap under the funnel is closed! Now you can start opening the flap and let your powder trickle into the transparent plastic receptacle under the glass funnel. If necessary, use the stirrer! When the powder is on the wraparound edge of the plastic receptacle, close the flap and measure the height of the cone. Repeat it five-times!

Mathematical Formula for Tamped Density:

$$\text{Arc tan}\left(2 * \frac{\text{height}}{\text{diameter}}\right)$$

2.3.3 Feeding-Rate into the Extruder

The feeding-rate of excipients powder into the feeder is evaluated with a real feeder of Brabender® Mini-Compounder KETSE 12/36 D)

2.3.4 Homogeneity with APIs

The present examples are carried out using poorly soluble active ingredients. Indomethacin is used here as a representative model substance. Indomethacin is in water a poorly soluble active ingredient [0,937 mg/L, at 25° C.].

The applied polymer [polyvinyl alcohol (PVA)] with different particle size and distribution is blended with 30% API (indomethacin) powder. Real concentration of indomethacin from different positions of the mixture is detected by NMR spectroscopy.

Determination of Indomethacin Content by NMR Spectroscopy

For determination of the Indomethacin content about 20 mg of sample and 20 mg of maleic acid are exactly weighted and dissolved in DMSO-d6. The clear solution is transferred into a 5 mm NMR tube. The 1H-NMR spectra are recorded on a 500 MHz Bruker Avance III spectrometer equipped with a cryo-cooled TCI probe. The FID is digitized by 128 K data points over a spectral width of 25 ppm. A total of 32 spectra are accumulated with a relaxation delay of 10 s between each scan. Prior to the Fourier transformation, the recorded FID is multiplied with an exponential function (lb=0.3 Hz). The phase and the baseline is corrected for the obtained spectrum.

For calculation of the Indomethacin content the resonance of the CH protons of maleic acid (ca. 6.3 ppm) and the CH protons of Indomethacin (e.g. 6.7 ppm, 6.9 ppm or 7.0 ppm) are integrated. The integral of maleic acid is set to 100. The content is calculated according to the general formula:

$$w_x[\%] = w_{St}[\%] \cdot \frac{z_{St} M_x I_x m_{St}}{z_x M_{St} I_{St} m_x}$$

$w_{St}$ [%]=content of standard in %
$z_{St}$=number of protons of standard contributing to the signal
$M_x$=molar mass of the compound of interest x
$I_x$=integral of the signal of the compound of interest x
$m_{St}$=weighted mass of the standard
$z_x$=number of protons of the compound of interest x contributing to the signal
$M_{St}$=molar mass of the standard
$I_{St}$=integral of the signal of the standard
$m_x$=weighted mass of the compound of interest x FIG. 1: shows a NMR spectrogram of 20 mg indomethacin and 20 mg maleic acid in DMSO-d6

3. Research Results 3.1 Particle Size and Distribution

Group A:

PVA4-88<45 µm: $D_{10}$=6.2 µm/$D_{50}$=27.99 µm/$D_{90}$=54.76 µm

A milled PVA powder of PVA 4-88 having this particle size distribution is characterized by the logarithmic plot of particle sizes ranging up to 100 microns to their volume percentage.

Figure 2:
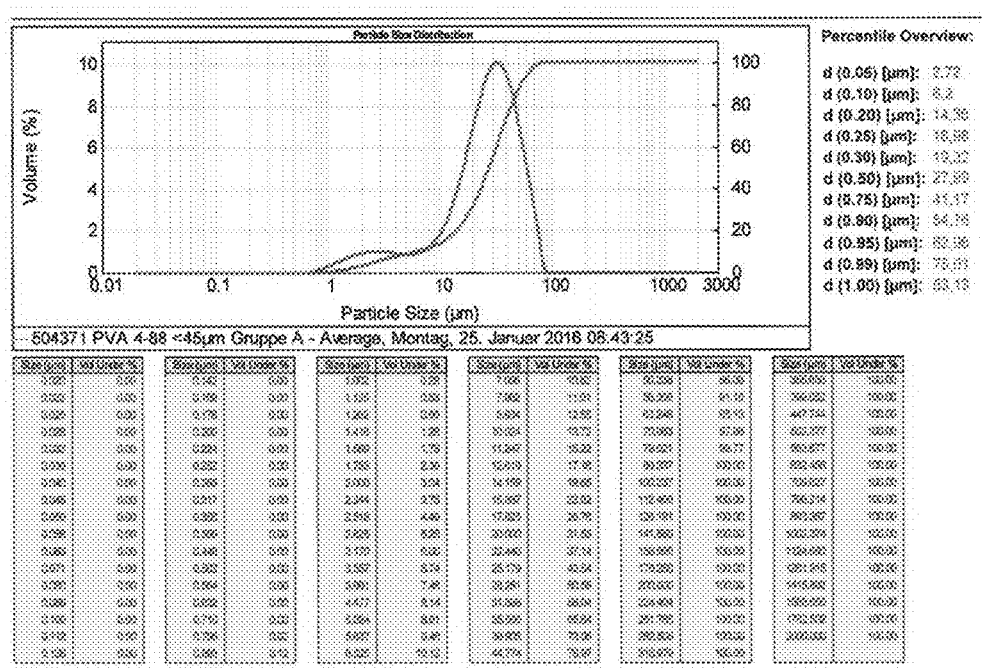
FIG. 2: shows the volume-particle size plot of PVA 4-88, having a particle size distribution of $D_{10}=6.2$ µm/$D_{50}=27.99$ µm/$D_{90}=54.76$ µm

FIG. 2: shows the volume-particle size plot of PVA 4-88, having a particle size distribution of $D_{10}$=6.2 µm/$D_{50}$=27.99 µm/$D_{90}$=54.76 µm Group B:

PVA4-88 45-1400 µm: $D_{10}$=17.25 µm/$D_{50}$=63.74 µm/$D_{90}$=169.91 µm

Figure 5:
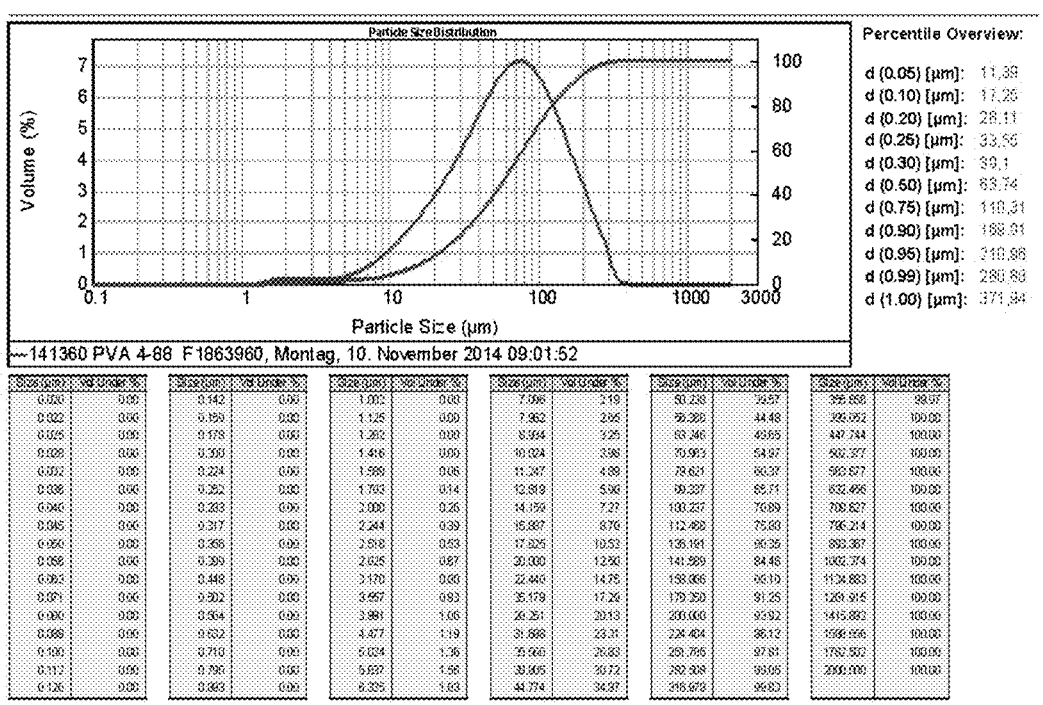
FIG. 5: shows the volume-particle size plot of PVA 4-88, having the advantageous particle size distribution of $D_{10}=17.25$ µm/$D_{50}=63.74$ µm/$D_{90}=169.91$ µm.

FIG. 5: shows the volume-particle size plot of PVA 4-88, having particle size distribution of $D_{10}$=17.25 µm/$D_{50}$=63.74 µm/$D_{90}$=169.91 µm 3.2 Flowability There are differences in the flowability, if PVA powders as characterized above (Group A, Group B and Group C) are compared with each other and there are additional effects in the flowability if the different PVA powders are mixed with APIs (Active Pharmaceutical Ingredients), so that flowabilities differ between mixtures with and without APIs.

Figure 3:
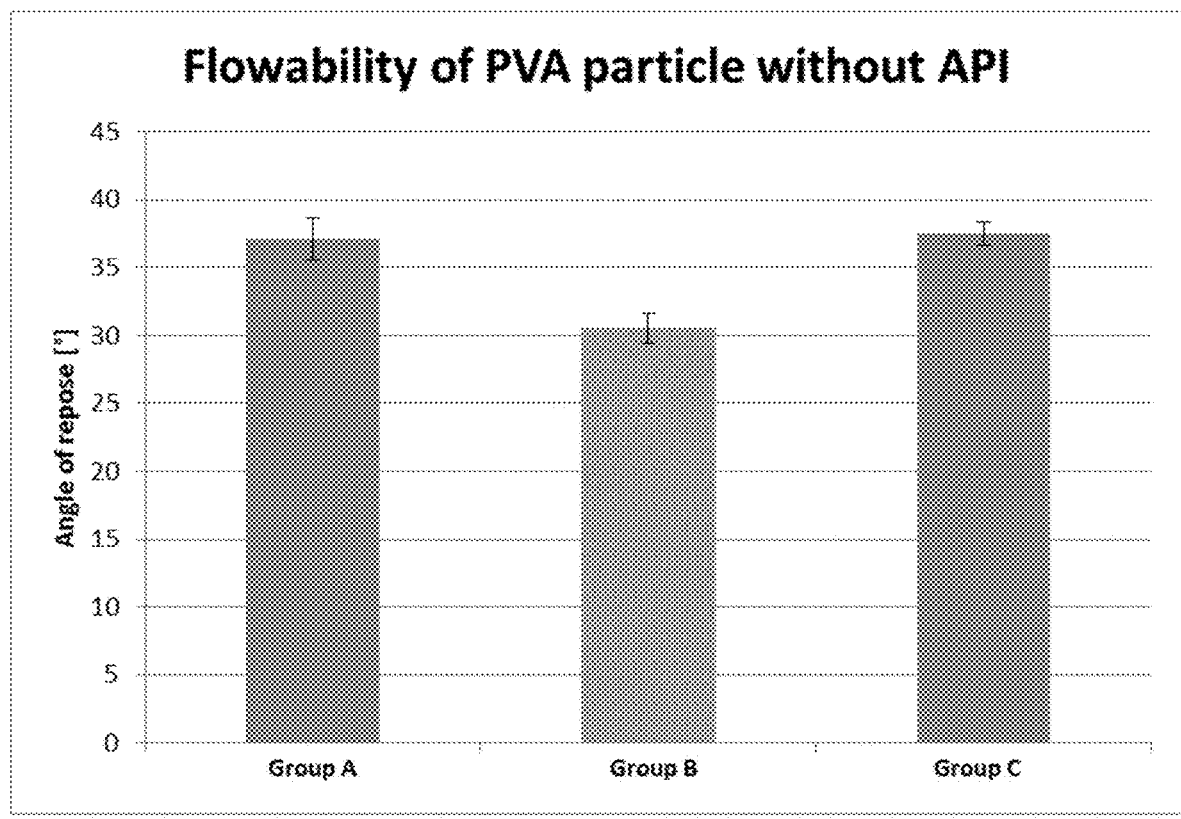
FIG. 3: shows the differences in the angles of repose of PVA powders of Groups A, B and C without the addition of any API

FIG. 3: shows the differences in the angles of repose of PVA powders of Groups A, B and C without the addition of any API 3.3 Results of Feeding-Rate

| Particle size | Load rate | without API (Maximum) | with API (30% Indomethacin) (Maximum) | Difference (Without API → With API) |
|---|---|---|---|---|
| Group A | 170 g/h | 1.157 kg/h | 1.189 kg/h | +0.032 kg/h |
| Group B | 170 g/h | Not determined! | 1.415 kg/h | — |
| Group C | 170 g/h | 3.246 kg/h | 1.951 kg/h | −1.295 kg/h |

Figure 4A:
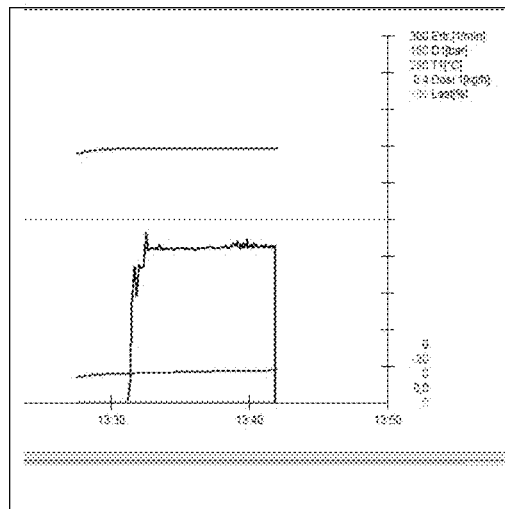
FIG. 4a: shows the feeding performance of PVA powder of Group A without API. The feeding is not uniform and shows irregularities.
Figure 4B:
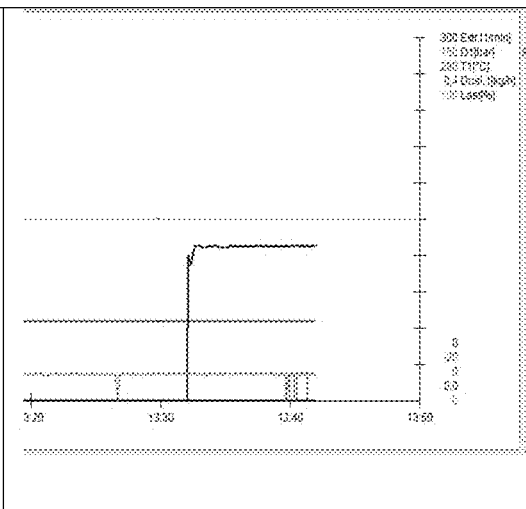
FIG. 4b: shows the feeding performance of PVA powder of Group A with 30% by weight of API. The feeding is not uniform and shows comparable irregularities as the feeding of the pure powder.
Figure 4C:
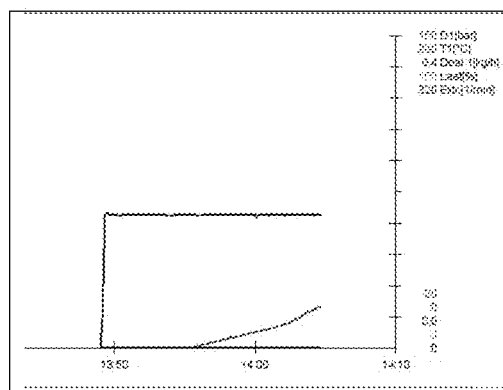
FIG. 4c: shows the feeding performance of PVA powder of Group B without API. The feeding is very uniform.

Feeding Performance:

In the figures FIG. 4a to FIG. 4c) the feeding rate of the PVA grades of Groups A and B is compared with and without addition of APIs. The comparison shows that the flowability of the powder without any API is also decisive for the flowability and on the uniformity of feeding rate of the blend with API.

FIG. 4a: shows the feeding performance of PVA powder of Group A without API. The feeding is not uniform and shows irregularities.

FIG. 4b: shows the feeding performance of PVA powder of Group A with 30% by weight of API. The feeding is not uniform and shows comparable irregularities as the feeding of the pure powder.

FIG. 4c: shows the feeding performance of PVA powder of Group B without API. The feeding is very uniform.

Figure 4D:
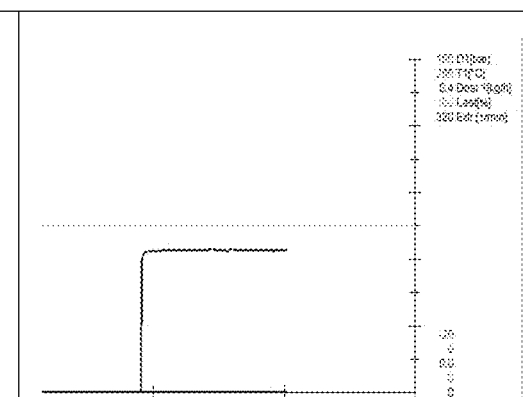
FIG. 4d: shows the feeding performance of PVA powder of Group B with 30% by weight of API. The feeding is also very uniform and is comparable to the feeding of the pure powder of Group B.

FIG. 4d: shows the feeding performance of PVA powder of Group B with 30% by weight of API. The feeding is also very uniform and is comparable to the feeding of the pure powder of Group B.

No diagram for PVA having mean particle size >1400 µm (Group C) could be performed, because the loading of these particles is not feasible!

The feeding rate is not determined, because the particles of the mixture are too large The particles are micronized in the feeder!
Loud grating in the feeder and danger that the feeder could be damaged!
Measurement had to be interrupted!

3.4 Homogeneity of Extrusion Mixtures with API

TABLE 1

Homogeneity of drug distribution in the extruded product

| Compounds | Concentration of indomethacin | Average | Error Bar |
|---|---|---|---|
| PVA4-88 <45 μm (Group A) + 30% Indomethacin | 31.10% 31.80% 31.40% 33.40% 31.20% 31.30% | 31.70% | 0.009 |
| PVA4-88 45-1400 μm (Group B) + 30% Indomethacin | 30.90% 31.00% 30.70% 31.80% 30.60% 30.00% | 30.83% | 0.006 |
| PVA4-88 >1400 μm (Group C) + 30% Indomethacin | 16.40% 25.10% 17.10% 17.60% 20.60% 26.10% | 20.48% | 0.042 |

The data of this table show that no homogeneous drug distribution in the extruded product can be obtained if a PVA powder is used having a particle size distribution of >1400 μm (Group C). In this case a separation of PVA particles and of API particles seems to occur before the mixture can be feed into the extruder.

3.5 Summary
Benefits of the Optimized Particle Size:
better flowability in the feeder with and without API
more homogenous
better results in analysis
equal distribution of the API in polymers→amorph
suitable particle size distribution and equal particles 4
improved tableting process The best cryo-milled PVA powders show the following particle size distribution:

| | D10 (μm) | D50 (μm) | D90 (μm) |
|---|---|---|---|
| Cryo-milled PVA | 17.25 | 63.74 | 169.91 |

FIG. 5: shows the volume-particle size plot of PVA 4-88, having the advantageous particle size distribution of $D_{10}=17.25$ μm/$D_{50}=63.74$ μm/$D_{90}=169.91$ μm.

Advantageous Properties of PVA Powders Having an Optimized Particle Size Distribution as Characterized Above:

The experiments show the relationship of the particle size distribution of PVA in relation to the flow properties as well as in relation to its suitability for its dosage into the feeder of an extrusion plant for hot melt extrusion.

By the experiments carried out it was found, that PVA powders having suitable particle sizes and size distributions can be used very well for hot melt extrusion excipients thanks to improved flow properties, their easy-to-load and good homogeneity with APIs and so on.

But PVA powders having particles larger than in this defined range cannot be continuously loaded into the feeder without any undesirable clumping and blocking of material supply in the feeder and the homogeneity of the API/PVA mixture is a problem due to the segregation of the comprised API. On the other hand, also particle size distributions, which are lower than the optimal size distributions found here, lead to issues with the flowability and to a blocking of the feeder.

In addition, PVA powders according to the present invention, which have in aqueous solution a viscosity* ≤40 mPa·s, show the advantage to be (hot) melt extrudable by themselves without the addition of any processing aids like additional plasticizer or other active ingredients (* viscosity is measured as 4.0% water solution at 20° C. DIN 53015).

However, PVA powders, which have in aqueous solution a viscosity* ≥40 mPa·s, need additional plasticizer or active ingredients as plasticizer to make the mixture extrudable.

What is claimed:

1. An extrudable polyvinyl alcohol (PVA) powder with improved flowability, consisting of particles consisting of PVA, which has been cryo-milled, and which has $d_{50}$ particle sizes in the range of 45 to 1400 μm.

2. An extrudable polyvinyl alcohol (PVA) powder with improved flowability, consisting of particles consisting of PVA, which has been cryo-milled, and which has a particle size distribution of $d_{10}=20\pm10$ μm, $d_{20}=30\pm10$ μm, $d_{50}=70\pm10$ μm, $d_{90}=200\pm30$ μm, and $d_{99}=300\pm30$ μm.

3. The polyvinyl alcohol according to claim 1, which has been extruded.

4. The polyvinyl alcohol according to claim 1 having a viscosity ≤40 mPa·s, the viscosity being measured on 4% w/v aqueous solution at 20° C. DIN 53015.

5. The polyvinyl alcohol according to claim 1, which is selected from the group consisting of PVA 3-88, PVA 4-88, PVA 5-74, PVA 5-88, PVA 8-88, and PVA 18-88.

6. The polyvinyl alcohol according to claim 1, which is capable of providing uninterrupted feeding and dosing during processing.

7. A powdery composition for the preparation of pharmaceutical formulations, comprising the polyvinyl alcohol according to claim 1 homogeneously mixed with at least one active pharmaceutical ingredient (API).

8. The powdery composition according to claim 7, comprising at least one additive selected from the group consisting of plasticizers, surface active materials, antioxidants, stabilizing agents, solubility-enhancing agents, pH control agents and flow regulators.

9. The powdery composition according to claim 7, which is a pharmaceutical grade powder comprising one or more further excipient(s) with $d_{50}$ particle sizes in the range of 45 μm to 1400 μm.

10. The powdery composition according to claim 7, which is a pharmaceutical grade powder comprising one or more further excipient(s) having a particle size distribution of $d_{10}=20\pm10$ μm, $d_{20}=30\pm10$ μm, $d_{50}=70\pm10$ μm, $d_{90}=200\pm30$ μm, $d_{99}=300\pm30$ μm.

11. A process for producing a solid pharmaceutical dosage form, comprising extruding or forming a homogenous melt of a mixture of ingredients comprising the cryo-milled powdered polyvinyl alcohol according to claim 1 and at least one active pharmaceutical ingredient (API), and forming a powder or a molded form.

12. The process according to claim 11, comprising continuously and evenly feeding the mixture of ingredients into a feeder line of an extruder, processing said mixture to a homogeneous melt, and then shaping the melt.

13. A process for producing a solid pharmaceutical dosage form according to claim 11, comprising
a) cryo-milling the polyvinyl alcohol (PVA) to a powder having $d_{50}$ particle sizes in the range of 45 to 1400 μm, and
b) homogeneously mixing the resultant powder with at least one active pharmaceutical ingredient, and optionally with at least one additive selected from the group consisting of plasticizers, surface active materials, antioxidants, stabilizing agents, solubility-enhancing agents, pH control agents and flow regulators, thereby forming a powdery composition, and
c) evenly feeding said composition into a feeder line of an extruder followed by processing to a homogeneous melt, and shaping.

14. A process according to claim 11, wherein the polyvinyl alcohol (PVA) is cryo-milled to a powder having a particle size distribution of $d_{10}=20\pm10$ μm, $d_{20}=30\pm10$ μm, $d_{50}=70\pm10$ μm, $d_{90}=200\pm30$ μm, and $d_{99}=300\pm30$ μm.

15. A process according to claim 11, wherein the polyvinyl alcohol (PVA) has a viscosity ≤40 mPa·s, the viscosity being measured on 4% w/v aqueous solution at 20° C. DIN 53015, and which is cryo-milled to a powder having a particle size distribution of $d_{10}=20\pm10$ μm, $d_{20}=30\pm10$ μm, $d_{50}=70\pm10$ μm, $d_{90}=200\pm30$ μm, and $d_{99}=300\pm30$ μm, and wherein optionally the particle size distribution is adjusted by combining respective sieve fractions.

16. A process according to claim 11, wherein the polyvinyl alcohol (PVA) is selected from the group consisting of PVA 3-88, PVA 4-88, PVA 5-74, PVA 5-88, PVA 8-88, and PVA 18-88, and which is cryo-milled to a powder having a particle size distribution of $d_{10}=20\pm10$ μm, $d_{20}=30\pm10$ μm, $d_{50}=70\pm10$ μm, $d_{90}=200\pm30$ μm, and $d_{99}=300\pm30$ μm, and wherein optionally the particle size distribution is adjusted by combining respective sieve fractions.

17. A solid pharmaceutical dosage form that has been obtained by the process according to claim 11.

18. A process for producing a solid pharmaceutical dosage form according to claim 12, comprising
a) cryo-milling the polyvinyl alcohol (PVA) to a powder having $d_{50}$ particle sizes in the range of 45 to 1400 μm, and
b) homogeneously mixing the resultant powder with at least one active pharmaceutical ingredient, and optionally with at least one additive selected from the group consisting of plasticizers, surface active materials, antioxidants, stabilizing agents, solubility-enhancing agents, pH control agents and flow regulators, thereby forming a powdery composition, and
c) evenly feeding said composition into a feeder line of an extruder followed by processing to a homogeneous melt, and shaping.

19. The polyvinyl alcohol according to claim 1, which has particle sizes in the range of 50 to 300 μm.

20. The polyvinyl alcohol according to claim 1, which has a particle size distribution of $d_{10}=20\pm10$ μm, $d_{50}=70\pm10$ μm and $d_{90}=200\pm30$ μm.

21. The polyvinyl alcohol according to claim 1, which has a particle size distribution of $d_{10}=17.25\pm10$ μm, $d_{50}=63.74\pm10$ μm and $d_{90}=169.91\pm30$ μm.

* * * * *